(12) United States Patent
Neuba et al.

(10) Patent No.: US 9,402,795 B2
(45) Date of Patent: *Aug. 2, 2016

(54) MULTI-TONAL ONE-STEP DYES

(71) Applicant: Henkel AG & Co. KGaA, Duesseldorf (DE)

(72) Inventors: Constanze Neuba, Grevenbroich (DE); Frank Janssen, Cologne (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/838,269

(22) Filed: Aug. 27, 2015

(65) Prior Publication Data

US 2015/0366772 A1  Dec. 24, 2015

Related U.S. Application Data

(63) Continuation of application No. PCT/EP2014/052041, filed on Feb. 3, 2014.

(30) Foreign Application Priority Data

Feb. 27, 2013 (DE) .......................... 10 2013 203 231

(51) Int. Cl.
  *A61Q 5/10*   (2006.01)
  *A61K 8/41*   (2006.01)
  *A61K 8/22*   (2006.01)
  *A61K 8/49*   (2006.01)

(52) U.S. Cl.
  CPC . *A61K 8/411* (2013.01); *A61K 8/22* (2013.01); *A61K 8/415* (2013.01); *A61K 8/494* (2013.01); *A61K 8/4953* (2013.01); *A61Q 5/10* (2013.01); *A61K 2800/4324* (2013.01); *A61K 2800/884* (2013.01)

(58) Field of Classification Search
  CPC ......... A61Q 5/10; A61K 8/411; A61K 8/415; A61K 8/494; A61K 8/4953; A61K 2800/884; A61K 2800/4324
  USPC ....................................... 8/405; 132/202, 208
  See application file for complete search history.

(56) References Cited

U.S. PATENT DOCUMENTS 3,210,252 A   10/1965  Blanke et al.

FOREIGN PATENT DOCUMENTS

DE   10037580 A1 *  8/2000  ............... A61Q 5/10
GB   2082207 A       3/1982

OTHER PUBLICATIONS

English translation (Apr. 8, 2016) of the Patent No. DE 10037580 A1.*
PCT International Search Report (PCT/EP2014/052041) dated Sep. 4, 2014.

* cited by examiner

*Primary Examiner* — Eisa Elhilo
(74) *Attorney, Agent, or Firm* — David K. Benson

(57) ABSTRACT

A cosmetic agent (A) is applied to the fibers and allowed to act for a time period from 30 seconds to 30 minutes. Then a cosmetic agent (B) is applied to the keratinic fibers still being acted upon by agent (A), and both agents (A) and (B) are allowed to act for a time period from 5 to 45 minutes, whereupon agents (A) and (B) are rinsed out. Agent (A) (a1) contains one or more oxidation dye precursors of the developer type, (a2) does not contain an oxidation dye precursor of the coupler type, (a3) has a pH from 8.0 to 12.0, and agent (B) (b1) contains one or more oxidation dye precursors, (b2) contains one or more oxidizing agents, and (b3) has a pH from 8.0 to 12.0.

15 Claims, No Drawings

MULTI-TONAL ONE-STEP DYES

FIELD OF THE INVENTION

The present invention generally relates to a method for treating keratinic fibers, which makes it possible to color hair in one dyeing step and simultaneously to produce a multi-tonal color with lighter ("highlights") or darker ("lowlights") sections (small strands).

BACKGROUND OF THE INVENTION

Over time and particularly with exposure to external influences such as light or harmful atmospheric substances, hair loses or changes its natural color and its shine or luster. For this reason, hair coloring agents are widely used either at hair salons or at home. So-called oxidation coloring agents are used for permanent, intensive colors with suitable fastness properties. Such coloring agents typically contain oxidation dye precursors, so-called developer components and coupler components, which under the influence of oxidizing agents or atmospheric oxygen form the actual dyes with one another. The oxidation coloring agents are characterized by excellent, long-lasting coloring results. Coloring or tinting agents, containing so-called substantive dyes ("direct dyes") as the coloring component, are typically used for temporary colors. Apart from dyeing, the lightening of the natural hair color or dyeing the hair a blond color is the very specific wish of many consumers, because a blond hair color is regarded as attractive and fashionably desirable. If substrates are to be lightened or even bleached, the dyes coloring the substrate are mostly decolorized with the use of appropriate oxidizing agents, such as hydrogen peroxide.

In hair dyeing, particularly in hair dyeing at home, the problem arises that natural color nuances are completely covered, so that multi-tonal colors are difficult to realize.

To give the hair a more natural appearance, it is proposed to partially decolorize dyed hair by the selective use of oxidizing agents. Hair sections ("small strands") to which the oxidizing agents are applied thereby bleach out at least partially, resulting in a multi-tonal hair color. The oxidizing agent is applied thereby with a brush or applicator, whereby hair not to be treated is protected from decolorizing optionally by aluminum foil or a so-called "highlighting cap."

This type of application does in fact solve the problem of the most possible natural dyeing of hair, but allows only the placing of "highlights." The hair must be dyed again to achieve "lowlights," i.e., darker sections. In each of the cases, a time-consuming second decolorizing or dyeing step is necessary, which follows the original dyeing. In particular in use at home, therefore, the entire hair must first be colored before the consumer can place "highlights" or "lowlights." Many consumers regard this as time-consuming and also frustrating, because the essential color-changing step occurs at the beginning and is "corrected" in a second step.

It is therefore desirable to provide a method that enables multi-tonal dyeing in a single coloring step. In this regard, the dyeing of the hair with the production of "highlights" or "lowlights" should proceed so that a result is visible immediately after the coloring agent is rinsed out.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A method for the oxidative dyeing of keratinic fibers, comprising the steps A) applying a cosmetic agent (A) to the fibers; B) allowing agent (A) to act for a time period from 30 seconds to 30 minutes; C) applying a cosmetic agent (B) to the keratinic fibers still being acted upon by agent (A); D) allowing both agents (A) and (B) to act for a time period from 5 to 45 minutes; E) rinsing out of agents (A) and (B), characterized in that agent (A) (a1) contains one or more oxidation dye precursors of the developer type; (a2) does not contain an oxidation dye precursor of the coupler type; (a3) has a pH from 8.0 to 12.0; agent (B) (b1) contains one or more oxidation dye precursors; (b2) contains one or more oxidizing agents; and (b3) has a pH from 8.0 to 12.0.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now been found that a partial pretreatment of fiber areas or small strands has the result that this area or small strands are dyed more intensively or less intensively later. By pre-penetrating individual fiber areas or small strands, the coloring agent used immediately thereafter colors the hair multi-tonally, and the consumer can admire a natural dyeing result with "highlights" or "lowlights" immediately after the dyeing step.

The subject of the present invention in a first embodiment is a method for the oxidative dyeing of keratinic fibers, comprising the steps:

A) applying a cosmetic agent (A) to the fibers,
B) allowing agent (A) to act for a time period from 30 seconds to 30 minutes,
C) applying a cosmetic agent (B) to the keratinic fibers still being acted upon by agent (A),
D) allowing both agents (A) and (B) to act for a time period from 5 to 45 minutes,
E) rinsing out agents (A) and (B),
in which agent (A)
(a1) contains one or more oxidation dye precursors of the developer type,
(a2) does not contain an oxidation dye precursor of the coupler type,
(a3) has a pH from 8.0 to 12.0,
agent (B)
(b1) contains one or more oxidation dye precursors,
(b2) contains one or more oxidizing agents, and
(b3) has a pH from 8.0 to 12.0.

In the first step of the method according to the invention, a cosmetic agent (A) is applied to the fibers. Said agent (A), which is also called a pretreatment agent or a prepenetrating agent below, is left on the keratinic fibers for a period of 30 seconds to 30 minutes (step B) of the method according to the invention). Methods preferred according to the invention are characterized by rather shorter treatment times of the pretreatment agent. Especially preferred methods according to the invention are characterized in that agent (A) in step B) is allowed to act on the fibers for a time period from 30 seconds to 15 minutes, preferably from 30 seconds to 10 minutes, and especially preferably from 30 seconds to 5 minutes.

To achieve multi-tonal dyeing, agent (A) should not be applied uniformly to the keratinic fibers. Preferably, only individual regions, especially preferably only individual strands are treated with agent (A). Alternatively, the concentration of agent A on the small individual strands can be varied. It is also possible to first treat all keratinic fibers uniformly with agent (A) and then to treat individual regions again with agent (A). A repeated treatment of individual regions/strands with agent (A) is also possible according to the invention.

Especially preferred methods according to the invention are characterized in that the application of cosmetic agent (A) to the fibers in step A) occurs only to individual small strands.

Especially preferred methods according to the invention furthermore are characterized by
B) allowing agent (A) to act for a time period from 2 to 10 minutes at a temperature from 20 to 60° C., preferably from 25 to 55° C., more preferably from 27 to 50° C., and very especially preferably from 30 to 45° C.

After the treatment time of the pretreatment agent, the keratinic fibers are not rinsed out or toweled off. Rather, in step C) of the method according to the invention, a cosmetic agent (B) is applied to the fibers still being acted on by agent (A). The mixture of agents (A) and (B), formed by the application of agent (B) to the keratinic fibers, in step D) of the method according to the invention is allowed to act for a time period from 5 to 45 minutes.

The methods preferred according to the invention are characterized by shorter treatment times of the mixture of agents (A) and (B). Especially preferred methods according to the invention are characterized in that agents (A) and (B) in step D) are allowed to act for a time period from 5 to 30 minutes, preferably from 5 to 20 minutes, especially preferably from 5 to 15 minutes.

The treatment times mentioned last in this case refer to the mixture of agents (A) and (B). Because agent (A) in step B) of the method according to the invention has already acted, the fibers have a longer contact overall with the ingredients of agent (A) than with those of agent (B). If agent (A) was applied only to individual small strands or in individual areas, the ingredients of agent (A) could act more intensively in these regions and thus intensify or weaken the effect of the ingredients of agent (B) in these regions, as a result of which a darker and lighter color of these regions is achieved.

After agents (A) and (B) are rinsed out in step E) of the method according to the invention, the user immediately has a multi-tonal color experience, without having to perform a further step.

According to the invention, agent (A) contains one or more oxidation dye precursors of developer type (a1) and is free of oxidation dye precursors of coupler type (a2).

Preferred oxidation dye precursors of the developer type are p-phenylenediamine derivatives. Preferred p-phenylenediamines are selected from one or more compounds from the group comprising p-phenylenediamine, p-toluylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis(2-hydroxyethyl)-p-phenylenediamine, 4-N,N-bis(2-hydroxyethyl)amino-2-methylaniline, 4-N,N-bis(2-hydroxyethyl) amino-2-chloroaniline, 2-(2-hydroxyethyl)-p-phenylenediamine, 2-(1,2-dihydroxyethyl)-p-phenylenediamine, 2-fluoro-p-phenylenediamine, 2-isopropyl-p-phenylenediamine, N-(2-hydroxypropyl)-p-phenylenediamine, 2-hydroxymethyl-p-phenylenediamine, N,N-dimethyl-3-methyl-p-phenylenediamine, N-ethyl-N-2-hydroxyethyl-p-phenylenediamine, N-(2,3-dihydroxypropyl)-p-phenylenediamine, N-(4'-aminophenyl)-p-phenylenediamine, N-phenyl-p-phenylenediamine, 2-(2-hydroxyethyloxy)-p-phenylenediamine, 2-methoxymethyl-p-phenylenediamine, 2-(2-acetylaminoethyloxy)-p-phenylenediamine, N-(2-methoxyethyl)-p-phenylenediamine, N-(4-amino-3-methylphenyl)-N-[3-(1H-imidazol-1-yl)propyl]amine, 5,8-diaminobenzo-1,4-dioxane, and the physiologically acceptable salts thereof. p-Phenylenediamine derivatives especially preferred according to the invention are selected from at least one compound from the group comprising p-phenylenediamine, p-toluylenediamine, 2-(2-hydroxyethyl)-p-phenylenediamine, 2-(1,2-dihydroxyethyl)-p-phenylenediamine, N,N-bis(2-hydroxyethyl)-p-phenylenediamine, N-(4-amino-3-methylphenyl)-N-[3-(1H-imidazol-1-yl)propyl]amine, 2-methoxymethyl-p-phenylenediamine, and the physiologically acceptable salts thereof. It can be preferable furthermore according to the invention to use as a developer component compounds that contain at least two aromatic rings substituted with amino and/or hydroxyl groups. Preferred binuclear developer components are selected in particular from at least one of the following compounds: N,N'-bis(2-hydroxyethyl)-N,N'-bis(4'-aminophenyl)-1,3-diaminopropan-2-ol, N,N'-bis(2-hydroxyethyl)-N,N'-bis(4'-aminophenyl)ethylenediamine, N,N'-bis(4'-aminophenyl)tetramethylenediamine, N,N'-bis(2-hydroxyethyl)-N,N'-bis(4'-aminophenyl)tetramethylenediamine, N,N'-bis(4-(methylamino)phenyl)tetramethylenediamine, N,N'-diethyl-N,N'-bis(4'-amino-3'-methylphenyl)ethylenediamine, bis(2-hydroxy-5-aminophenyl) methane, N,N'-bis(4'-aminophenyl)-1,4-diazacycloheptane, N,N'-bis(2-hydroxy-5-aminobenzyl)piperazine, N-(4'-aminophenyl)-p-phenylenediamine, and 1,10-bis(2',5'-diaminophenyl)-1,4,7,10-tetraoxadecane, and physiologically acceptable salts thereof. Very especially preferred binuclear developer components are selected from among N,N'-bis(2-hydroxyethyl)-N,N'-bis(4-aminophenyl)-1,3-diaminopropan-2-ol, bis(2-hydroxy-5-aminophenyl)methane, 1,3-bis(2,5-diaminophenoxy)propan-2-ol, N,N'-bis(4-aminophenyl)-1,4-diazacycloheptane, 1,10-bis(2,5-diaminophenyl)-1,4,7,10-tetraoxadecane, or one of the physiologically acceptable salts thereof. It can be preferred furthermore according to the invention to use a p-aminophenol derivative or one of the physiologically acceptable salts thereof as a developer component. Preferred p-aminophenols are in particular p-aminophenol, N-methyl-p-aminophenol, 4-amino-3-methylphenol, 4-amino-3-fluorophenyl, 2-hydroxymethylamino-4-aminophenol, 4-amino-3-hydroxymethylphenol, 4-amino-2-(2-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(2-hydroxyethylaminomethyl)phenol, 4-amino-2-(1,2-dihydroxyethyl)phenol, 4-amino-2-fluorophenol, 4-amino-2-chlorophenol, 4-amino-2,6-dichlorophenol, 4-amino-2-(diethylaminomethyl)phenol, and physiologically acceptable salts thereof. Very especially preferred compounds are p-aminophenol, 4-amino-3-methylphenol, 4-amino-2-aminomethylphenol, 4-amino-2-(1,2-dihydroxyethyl)phenol, and 4-amino-2-(diethylaminomethyl)phenol. Further, the developer component can be selected from among o-aminophenol and derivatives thereof, such as 2-amino-4-methylphenol, 2-amino-5-methylphenol, or 2-amino-4-chlorophenol. Furthermore, the developer component can be selected from among heterocyclic developer components, such as pyrimidine derivatives, pyrazole derivatives, pyrazolopyrimidine and pyrazolopyrazole derivatives, or physiologically acceptable salts thereof. Preferred pyrimidine derivatives are in particular the compounds: 2,4,5,6-tetraaminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine, and 2,5,6-triaminopyrimidine. Preferred pyrazole derivatives are in particular the compounds, selected from among 4,5-diamino-1-methylpyrazole, 4,5-diamino-1-(2-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-t-butyl-1-methylpyrazole, 4,5-diamino-1-t-butyl-3-methylpyrazole, 4,5-diamino-1-(2-hydroxyethyl)-3-methylpyrazole, 4,5-diamino-1-ethyl-3-methylpyrazole, 4,5-diamino-1-ethyl-3-(4-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2-aminoethyl)amino-1,3-dimethylpyrazole, and the physiologically acceptable salts thereof, but particularly 4,5-diamino-1-(2-hydroxyethyl) pyrazole. Preferred pyrazolopyrimidines are the compounds, selected from among pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a] pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 3-amino-7-dimethylamino-2,5-dimethylpyrazolo[1,5-a]pyrimidine, and the physiologically acceptable salts thereof and the tautomeric forms thereof, if a tautomeric equilibrium is present. A preferred pyrazolopyrazole derivative is 2,3-diamino-6,7-dihydro-1H,5H-pyrazolo[1,2-a]pyrazol-1-one.

Especially preferred developer components are selected from at least one compound from the group comprising p-phenylenediamine, p-toluylenediamine, 2-(2-hydroxyethyl)-p-phenylenediamine, 2-(1,2-dihydroxyethyl)-p-phenylenediamine, N,N-bis(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis(2-hydroxyethyl)-N,N'-bis(4-aminophenyl)-1,3-diaminopropan-2-ol, bis(2-hydroxy-5-aminophenyl)methane, 1,3-bis(2,5-diaminophenoxy)propan-2-ol, N,N'-bis(4-aminophenyl)-1,4-diazacycloheptane, 1,10-bis(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, and the physiologically acceptable salts thereof. Very especially preferred developer components are p-toluylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)pyrazole, and the physiologically acceptable salts thereof.

It turned out that certain oxidation dye precursors of the developer type in certain amounts are especially highly suitable for use in the pretreatment agent (A) and when used they result in especially vibrant, colorfast, rub-resistant, sweat-resistant, and UV-resistant multi-tonal colors.

Especially preferred methods according to the invention are characterized in that agent (A) contains as an oxidation dye precursor of the developer type (a1) one or more compounds from the group comprising p-phenylenediamine, p-toluylenediamine, 2-(2-hydroxyethyl)-p-phenylenediamine, 2-(1,2-dihydroxyethyl)-p-phenylenediamine, N,N-bis(2-hydroxyethyl)-p-phenylenediamine, 2-methoxymethyl-p-phenyldiamine, N-(4-amino-3-methylphenyl)-N-[3-(1H-imidazol-1-yl)propyl]amine, and/or the physiologically acceptable salts thereof in a total amount from 0.1 to 3.5% by weight, preferably from 0.3 to 2.8% by weight, more preferably from 0.4 to 2.1% by weight, and especially preferably from 0.5 to 1.6% by weight, based on the total weight of agent (A).

Further especially preferred methods according to the invention are characterized in that agent (A) contains as an oxidation dye precursor of the developer type (a1) one or more compounds from the group comprising bis(2-hydroxy-5-aminophenyl)methane, 1,3-bis(2,5-diaminophenoxy)propan-2-ol, N,N'-bis(4-aminophenyl)-1,4-diazacycloheptane, 1,10-bis(2,5-diaminophenyl)-1,4,7,10-tetraoxadecane, p-aminophenol, 4- and amino-3-methylphenol, and/or the physiologically acceptable salts thereof in a total amount from 0.1 to 3.5% by weight, preferably from 0.3 to 2.8% by weight, more preferably from 0.4 to 2.1% by weight, and especially preferably from 0.5 to 1.6% by weight, based on the total weight of agent (A).

Further especially preferred methods according to the invention are characterized in that agent (A) contains as an oxidation dye precursor of the developer type (a1) one or more compounds from the group comprising 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, and/or the physiologically acceptable salts thereof in a total amount from 0.1 to 3.5% by weight, preferably from 0.3 to 2.8% by weight, more preferably from 0.4 to 2.1% by weight, and especially preferably from 0.5 to 1.6% by weight, based on the total weight of agent (A).

Further especially preferred methods according to the invention are characterized in that agent (A) contains as oxidation dye precursors of developer type (a1) at least one of the following combinations: p-toluylenediamine/2-(2-hydroxyethyl)-p-phenylenediamine; p-toluylenediamine/2-methoxymethyl-p-phenylenediamine; p-toluylenediamine/N,N-bis(2-hydroxyethyl)-p-phenylenediamine; p-toluylenediamine/2-methoxymethyl-p-phenylenediamine; p-toluylenediamine/N-(4-amino-3-methylphenyl)-N-[3-(1H-imidazol-1-yl)propyl]amine; p-toluylenediamine/bis(2-hydroxy-5-aminophenyl)methane; p-toluylenediamine/4- and amino-3-methylphenol; p-toluylenediamine/4,5-diamino-1-(2-hydroxyethyl)pyrazole; p-toluylenediamine/2,4,5,6-tetraaminopyrimidine; 2-(2-hydroxyethyl)-p-phenylenediamine/2-methoxymethyl-p-phenylenediamine; 2-(2-hydroxyethyl)-p-phenylenediamine/N,N-bis(2-hydroxyethyl)-p-phenylenediamine; 2-(2-hydroxyethyl)-p-phenylenediamine/2-methoxymethyl-p-phenylenediamine; 2-(2-hydroxyethyl)-p-phenylenediamine/N-(4-amino-3-methylphenyl)-N-[3-(1H-imidazol-1-yl)propyl]amine; 2-(2-hydroxyethyl)-p-phenylenediamine/bis(2-hydroxy-5-aminophenyl)methane; 2-(2-hydroxyethyl)-p-phenylenediamine/4-amino-3-methylphenol; 2-(2-hydroxyethyl)-p-phenylenediamine/4,5-diamino-1-(2-hydroxyethyl)pyrazole; 2-(2-hydroxyethyl)-p-phenylenediamine/2,4,5,6-tetraaminopyrimidine; 2-methoxymethyl-p-phenylenediamine/2-(2-hydroxyethyl)-p- phenylenediamine; 2-methoxymethyl-p-phenylenediamine/ 2-methoxymethyl-p-phenylenediamine; 2-methoxymethyl-p-phenylenediamine/N,N-bis(2-hydroxyethyl)-p-phenylenediamine; 2-methoxymethyl-p-phenylenediamine/ 2-methoxymethyl-p-phenylenediamine; 2-methoxymethyl-p-phenylenediamine/N-(4-amino-3-methylphenyl)-N-[3 [(1H-imidazol-1-yl)propyl]amine; 2-methoxymethyl-p-phenylenediamine/bis(2-hydroxy-5-aminophenyl)methane; 2-methoxymethyl-p-phenylenediamine/4-amino-3-methylphenol; 2-methoxymethyl-p-phenylenediamine/4,5-diamino-1-(2-hydroxyethyl)pyrazole; 2-methoxymethyl-p-phenylenediamine/2,4,5,6-tetraaminopyrimidine, and/or 4- and amino-3-methylphenol/4,5-diamino-1-(2-hydroxyethyl) pyrazole, and/or the physiologically acceptable salts thereof.

The pretreatment agent (A) has a pH from 8.0 to 12.0 (a3). Preferred methods according to the invention are characterized in that agent (A) has a pH (a3) from 8.5 to 11.5, preferably from 8.8 to 11.0, more preferably from 9.0 to 10.8, and especially preferably from 9.2 to 10.5.

In addition to the oxidation dye precursor(s) of the developer type, agent (A) used in the method according to the invention can contain further ingredients. Here, alkalinizing agents in particular have proven to be especially suitable.

Organic alkalinizing agents that can be used according to the invention are preferably selected from alkanolamines of primary, secondary, or tertiary amines with a $C_2$-$C_6$ alkyl parent structure, bearing at least one hydroxyl group. Very especially preferred alkanolamines according to the invention are selected from the group comprising 2-aminoethan-1-ol (monoethanolamine), 2-amino-2-methylpropan-1-ol, and 2-amino-2-methylpropane-1,3-diol. An especially preferred alkanolamine is monoethanolamine. Suitable basic amino acids are lysine, arginine, and ornithine. The inorganic alkalinizing agents according to the invention are preferably selected from the group comprising sodium hydroxide, potassium hydroxide, calcium hydroxide, barium hydroxide, sodium phosphate, potassium phosphate, sodium silicate, potassium silicate, sodium carbonate, and potassium carbonate.

Methods especially preferred according to the invention are characterized in that agent (A) contains one or more alkalinizing agents from the group comprising sodium hydroxide, potassium hydroxide, ammonia, monoethanolamine, and 2-amino-2-methylpropanol in a total amount from 0.3 to 4.5% by weight, preferably from 0.5 to 3.5% by weight, more preferably from 0.7 to 2.5% by weight, and especially preferably from 0.9 to 1.5% by weight, based on the total weight of agent (A).

A higher viscosity of the agent has proven advantageous to be able to apply the prepenetrating agent (A) in a clean and locally limited manner. It is advantageous to this end, if the agent is not a paste, viscous cream, or thickened gel, but has a sufficient flowability. Furthermore, the ready-to-use agent must in fact have rheological properties, which allow application onto fibers to be colored, but simultaneously prevent the agent from running off or flowing away from the site of action during the application period. Agents (A) therefore preferably have a viscosity from 5 to 100 Pa·s, preferably from 10 to 50 Pa·s, particularly from 10 to 20 Pa·s, and especially preferably from 10 to 16 Pa·s (Brookfield, 22° C., spindle #5, 4 rpm). To this end, preferred agents (A) contain at least one thickener and/or at least one gelling agent. Corresponding methods according to the invention, in which agent (A) contains in addition at least one thickener and/or at least one gelling agent, are preferred according to the invention.

A further very especially preferred embodiment is characterized in that the prepenetrating agent (A) has a viscosity from 5000 to 12,000 mPas, preferably from 5500 to 11,000 mPas, more preferably from 6000 to 10,000 mPas, and very especially preferably from 6500 to 9500 mPas (Brookfield, 22° C., spindle #5, 4 rpm).

Especially preferred prepenetrating agents (A) in a further embodiment are therefore characterized in that they contain at least one anionic polymeric thickener. Preferred anionic polymeric thickeners are selected from crosslinked or non-crosslinked copolymers, which contain at least two different monomers from the group comprising acrylic acid, methacrylic acid, $C_1$-$C_6$ alkyl esters of acrylic acid, and/or $C_1$-$C_6$ alkyl esters of methacrylic acid.

Especially preferred anionic copolymers are copolymers of acrylic acid, methacrylic acid, or the $C_1$-$C_6$ alkyl esters thereof, which are marketed under the INCI name of Acrylates Copolymer. Preferred in particular is the combination of methacrylic acid and ethyl acrylate and optionally crosslinked, multifunctional monomers. A preferred commercial product for this is, for example, Aculyn® 33 or 33A, which is sold by the company Rohm & Haas.

As further preferred thickeners, the prepenetrating agent (A) can contain one or more anionic polymeric thickeners from the group comprising xanthans, alginates, carboxyalkylcelluloses, and hyaluronic acids.

Xanthan is an anionic polysaccharide, which is made up of, inter alia, the structural components: D-glucose, D-mannose, D-glucuronic acid, acetate, and pyruvate, and is also known under the INCI name Xanthan Gum.

Salts of alginic acid are called alginates (INCI name Algin). Alginates are acidic, carboxy group-containing polysaccharides, consisting of D-mannuronic acid and D-guluronic acid in different ratios, which are linked by 1-4-glycosidic bonds. Both the alkaline and alkaline earth salts of alginic acids are novel. The use of alginic acid, sodium alginate, potassium alginate, ammonium alginate, and/or calcium alginate in the agents according to the invention has proven especially advantageous.

Carboxyalkylcelluloses are cellulose ethers in which the hydrogen atoms of the hydroxy groups of the cellulose are partially or completely substituted by carboxyalkyl groups. A preferred carboxyalkylcellulose is carboxymethylcellulose, which preferably can be used as an anionic polymer in the form of its sodium salt (sodium carboxymethylcellulose).

The basic structural unit of hyaluronic acid (INCI names: Hyaluronic acid, Sodium Hyaluronate) is an amino disaccharide which is made up of D-glucuronic acid and N-acetylglucosamine in a 1-3-glycosidic bond and is connected to the next unit with a β-1-4-glycosidic bond. Sodium and potassium salts of hyaluronic acid within the scope of research leading to this invention have proven especially suitable for producing intensively coloring dye formulations optimized with respect to their viscosity.

A further very especially preferred embodiment is characterized in that the prepenetrating agent (A) contains one or more anionic polymeric thickeners from the group of copolymers of acrylic acid and $C_1$-$C_6$ alkyl esters, the copolymers of methacrylic acid and $C_1$-$C_6$ alkyl esters, xanthan, and carboxymethylcellulose.

The anionic polymeric thickeners can be used preferably in a total amount from 0.1 to 15% by weight, more preferably from 1 to 10% by weight, and especially from 1.5 to 7.5% by weight, whereby the amounts are based on the total weight of the prepenetrating agent (A).

In order to allow the natural and multi-tonal color result to emerge especially noticeably and surprisingly at the end of the method according to the invention, the pretreatment agent (A) is preferably not capable of being used by itself as a separate bleaching, lightening, or coloring agent. It is of particular advantage for this purpose, if the ready-to-use agents (A) are free of oxidizing agents, in particular are free of hydrogen peroxide and/or persulfates.

In this case, "free of" means that the agents contain no intentionally added compounds from the cited groups. Nevertheless, traces of these compounds can be introduced into the agents as contaminants or as minor components via other raw materials. "Free of" therefore means more specifically that the ready-to-use agents (A), based on their weight, contain less than 1% by weight, preferably less than 0.5% by weight, more preferably less than 0.25% by weight, even more preferably less than 0.1% by weight, and especially less than 0.01% by weight of the cited groups.

Methods preferred according to the invention are characterized in that agent (A) used in step A), based on its weight, contains less than 1% by weight, preferably less than 0.5% by weight, more preferably less than 0.25% by weight, even more preferably less than 0.1% by weight, and especially less than 0.01% by weight of hydrogen peroxide.

Further methods preferred according to the invention are characterized in that agent (A) used in step A), based on its weight, contains less than 1% by weight, preferably less than 0.5% by weight, more preferably less than 0.25% by weight, even more preferably less than 0.1% by weight, and especially less than 0.01% by weight of peroxo compounds.

Pretreatment agent (A) may contain further conventional ingredients; these will be described extensively below.

In step C) of the method according to the invention, a cosmetic agent (B) is applied to the keratinic fibers, still being acted upon by agent (A). Said agent (B) contains one or more oxidation dye precursors (b1) and one or more oxidizing agents (b2) and has a pH from 8.0 to 12.0.

Preferred agents (B) contain at least one oxidation dye precursor of the developer type. Corresponding methods according to the invention, in which agent (B) contains as an oxidation dye precursor (b1) one or more oxidation dye precursors of the developer type, are preferred according to the invention.

Suitable and preferred oxidation dye precursors of the developer type were already described further in detail above. The corresponding compounds can also be used with preference in agent (B). It turned out that certain oxidation dye precursors of the developer type in certain amounts are especially highly suitable for use in agent (B) and when used they result in especially vibrant, colorfast, rub-resistant, sweat-resistant, and UV-resistant multi-tonal colors.

Especially preferred methods according to the invention are characterized in that agent (B) contains as an oxidation dye precursor of the developer type one or more compounds from the group comprising p-phenylenediamine, p-toluylenediamine, 2-(2-hydroxyethyl)-p-phenylenediamine, 2-(1,2-dihydroxyethyl)-p-phenylenediamine, N,N-bis(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or the physiologically acceptable salts thereof in a total amount from 0.1 to 3.5% by weight, preferably from 0.3 to 2.8% by weight, more preferably from 0.4 to 2.1% by weight, and especially preferably from 0.5 to 1.6% by weight, based on the total weight of agent (B).

Further especially preferred methods according to the invention are characterized in that agent (B) contains as an oxidation dye precursor of the developer type one or more compounds from the group comprising bis(2-hydroxy-5-aminophenyl)methane, 1,3-bis(2,5-diaminophenoxy)propan-2-ol, N,N'-bis(4-aminophenyl)-1,4-diazacycloheptane, 1,10-bis(2,5-diaminophenyl)-1,4,7,10-tetraoxadecane, p-aminophenol, 4- and amino-3-methylphenol, and/or the physiologically acceptable salts thereof in a total amount from 0.1 to 3.5% by weight, preferably from 0.3 to 2.8% by weight, more preferably from 0.4 to 2.1% by weight, and especially preferably from 0.5 to 1.6% by weight, based on the total weight of agent (B).

Further especially preferred methods according to the invention are characterized in that agent (B) contains as an oxidation dye precursor of the developer type one or more compounds from the group comprising 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, and/or the physiologically acceptable salts thereof in a total amount from 0.1 to 3.5% by weight, preferably from 0.3 to 2.8% by weight, more preferably from 0.4 to 2.1% by weight, and especially preferably from 0.5 to 1.6% by weight, based on the total weight of agent (B).

Further especially preferred methods according to the invention are characterized in that agent (B) contains as oxidation dye precursors of the developer type at least one of the following combinations: p-toluylenediamine/2-(2-hydroxyethyl)-p-phenylenediamine; p-toluylenediamine/2-methoxymethyl-p-phenylenediamine; p-toluylenediamine/N,N-bis(2-hydroxyethyl)-p-phenylenediamine; p-toluylenediamine/2-methoxymethyl-p-phenylenediamine; p-toluylenediamine/N-(4-amino-3-methylphenyl)-N-[3-(1H-imidazol-1-yl)propyl]amine; p-toluylenediamine/bis(2-hydroxy-5-aminophenyl)methane; p-toluylenediamine/4- and amino-3-methylphenol; p-toluylenediamine/4,5-diamino-1-(2-hydroxyethyl)pyrazole; p-toluylenediamine/2,4,5,6-tetraaminopyrimidine; 2-(2-hydroxyethyl)-p-phenylenediamine/2-methoxymethyl-p-phenylenediamine; 2-(2-hydroxyethyl)-p-phenylenediamine/N,N-bis(2-hydroxyethyl)-p-phenylenediamine; 2-(2-hydroxyethyl)-p-phenylenediamine/2-methoxymethyl-p-phenylenediamine; 2-(2-hydroxyethyl)-p-phenylenediamine/N-(4-amino-3-methylphenyl)-N-[3-(1H-imidazol-1-yl)propyl]amine; 2-(2-hydroxyethyl)-p-phenylenediamine/bis(2-hydroxy-5-aminophenyl)methane; 2-(2-hydroxyethyl)-p-phenylenediamine/4-amino-3-methylphenol; 2-(2-hydroxyethyl)-p-phenylenediamine/4,5-diamino-1-(2-hydroxyethyl)pyrazole; 2-(2-hydroxyethyl)-p-phenylenediamine/2,4,5,6-tetraaminopyrimidine; 2-methoxymethyl-p-phenylenediamine/2-(2-hydroxyethyl)-p-phenylenediamine; 2-methoxymethyl-p-phenylenediamine/2-methoxymethyl-p-phenylenediamine; 2-methoxymethyl-p-phenylenediamine/N,N-bis(2-hydroxyethyl)-p-phenylenediamine; 2-methoxymethyl-p-phenylenediamine/2-methoxymethyl-p-phenylenediamine; 2-methoxymethyl-p-phenylenediamine/N-(4-amino-3-methylphenyl)-N-[3[(1H-imidazol-1-yl)propyl]amine; 2-methoxymethyl-p-phenylenediamine/bis(2-hydroxy-5-aminophenyl)methane; 2-methoxymethyl-p-phenylenediamine/4-amino-3-methylphenol; 2-methoxymethyl-p-phenylenediamine/4,5-diamino-1-(2-hydroxyethyl)pyrazole; 2-methoxymethyl-p-phenylenediamine/2,4,5,6-tetraaminopyrimidine, and/or 4- and amino-3-methylphenol/4,5-diamino-1-(2-hydroxyethyl)pyrazole, and/or the physiologically acceptable salts thereof.

Depending on the desire to provide a multi-tonal color with greatly or less greatly varying nuances, the oxidation dye precursors employed in agents (A) and (B) can differ from one another. For a multi-tonal color with a very natural effect and soft transitions, methods according to the invention are preferred in which agents (A) and (B) contain the same oxidation dye precursors of the developer type.

If greater contrasts are desired, which are manifested in a more vibrant multi-tonal color appearance, methods according to the invention have proven effective in which agents (A) and (B) contain different oxidation dye precursors of the developer type.

According to the invention, agent (B) furthermore preferably contains one or more oxidation dye precursors of the coupler type.

Coupler components alone during the oxidative dyeing cause no significant dyeing, but always require the presence of developer components. Therefore, it is preferred according to the invention that at least one developer component is used in addition when at least one coupler component is employed. Coupler components within the meaning of the invention permit at least one substitution of a chemical group of the coupler by the oxidized form of the developer component. In this regard, a covalent bond forms between the coupler and developer component.

Coupler components according to the invention are preferably selected as at least one compound from one of the following classes: m-aminophenol, o-aminophenol, m-diaminobenzene, o-diaminobenzene, and/or derivatives thereof; naphthalene derivatives with at least one hydroxy group; di- or trihydroxybenzene; pyridine derivatives; pyrimidine derivatives; certain indole derivatives and indoline derivatives; pyrazolone derivatives (for example, 1-phenyl-3-methylpyrazol-5-one); morpholine derivatives (for example, 6-hydroxybenzomorpholine or 6-aminobenzomorpholine); quinoxaline derivatives (for example, 6-methyl-1,2,3,4-tetrahydroquinoxaline), and mixtures of two or more compounds of one or more of these classes.

Preferred m-aminophenol coupler components are selected from at least one compound from the group comprising 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-diethylaminophenol, N-cyclopentyl-3-aminophenol, 1,3-dihydroxy-5-(methylamino)benzene, 3-ethylamino-4-methylphenol, 2,4-dichloro-3-aminophenol, and the physiologically acceptable salts thereof. Preferred m-diaminobenzene coupler components are selected from at least one compound from the group comprising m-phenylenediamine, 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis(2'-hydroxyethyl)aminobenzene, and the physiologically acceptable salts thereof. Preferred o-diaminobenzene coupler components are selected from at least one compound from the group comprising 3,4-diaminobenzoic acid and 2,3-diamino-1-methylbenzene, and the physiologically acceptable salts thereof. Preferred naphthalene derivatives with at least one hydroxy group are selected from at least one compound of the group comprising 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene, and 2,3-dihydroxynaphthalene. Preferred di- or trihydroxybenzenes and derivatives thereof are selected from at least one compound of the group comprising resorcinol, resorcinol monomethyl ether, 2-methylresorcinol, 5-methylresorcinol, 2,5-dimethylresorcinol, 2-chlororesorcinol, 4-chlororesorcinol, pyrogallol, and 1,2,4-trihydroxybenzene. Preferred pyridine derivatives are selected from at least one compound from the group comprising 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 3,4-diaminopyridine, 2-(2-methoxyethyl)amino-3-amino-6-methoxypyridine, 2-(4'-methoxyphenyl)amino-3-aminopyridine, and the physiologically acceptable salts thereof. Preferred pyrimidine derivatives are selected from at least one compound of the group comprising 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine, and 4,6-dihydroxy-2-methylpyrimidine, and the physiologically acceptable salts thereof. Preferred indole derivatives are selected from at least one compound of the group comprising 4-hydroxyindole, 6-hydroxyindole, and 7-hydroxyindole, and the physiologically acceptable salts thereof. Preferred indoline derivatives are selected from at least one compound from the group comprising 4-hydroxyindoline, 6-hydroxyindoline, and 7-hydroxyindoline, and the physiologically acceptable salts thereof.

Especially preferred coupler components according to the invention are selected from among 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)-amino]ethanol, 3-amino-4-(2-methoxyethoxy)-5-methylphenylamine, 1-amino-3-bis(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of said compounds or the physiologically acceptable salts thereof. Very especially preferred are resorcinol, 2-methylresorcinol, 5-amino-2-methylphenol, 3-aminophenol, 2-(2,4-diaminophenoxy)ethanol, 1,3-bis(2,4-diaminophenoxy)propane, 1-methoxy-2-amino-4-(2'-hydroxyethylamino)benzene, 2-amino-3-hydroxypyridine, and 1-naphthol and one of the physiologically acceptable salts thereof.

The coupler components are preferably used in an amount from 0.0001 to 0.5% by weight, preferably 0.001 to 0.2% by weight, in each case based on agent (B).

It turned out that certain oxidation dye precursors of the coupler type in certain amounts are especially highly suitable for use in coloring agent (B) and when used they result in especially vibrant, colorfast, rub-resistant, sweat-resistant, and UV-resistant multi-tonal colors.

Methods preferred according to the invention are therefore characterized in that agent (B) contains as an oxidation dye precursor of the coupler type one or more compounds from the group comprising 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, and/or the physiologically acceptable salts thereof in a total amount from 0.1 to 3.5% by weight, preferably from 0.3 to 2.8% by weight, more preferably from 0.4 to 2.1% by weight, and especially preferably from 0.5 to 1.6% by weight, based on the total weight of agent (B).

Further methods preferred according to the invention are characterized in that agent (B) contains as an oxidation dye precursor of the coupler type one or more compounds from the group comprising 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, and/or the physiologically acceptable salts thereof in a total amount from 0.1 to 3.5% by weight, preferably from 0.3 to 2.8% by weight, more preferably from 0.4 to 2.1% by weight, and especially preferably from 0.5 to 1.6% by weight, based on the total weight of agent (B).

Further methods preferred according to the invention are characterized in that agent (B) contains as an oxidation dye precursor of the coupler type one or more compounds from the group comprising resorcinol, 2-methylresorcinol, and/or 4-chlororesorcinol in a total amount from 0.1 to 3.5% by weight, preferably from 0.3 to 2.8% by weight, more preferably from 0.4 to 2.1% by weight, and especially preferably from 0.5 to 1.6% by weight, based on the total weight of agent (B).

Further methods preferred according to the invention are characterized in that agent (B) contains as an oxidation dye precursor of the coupler type one or more compounds from the group comprising 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, and/or the physiologically acceptable salts thereof in a total amount from 0.1 to 3.5% by weight, preferably from 0.3 to 2.8% by weight, more preferably from 0.4 to 2.1% by weight, and especially preferably from 0.5 to 1.6% by weight, based on the total weight of agent (B).

Further preferred methods according to the invention are characterized in that agent (B) contains as an oxidation dye precursor of the coupler type at least one of the following combinations: resorcinol/3-aminophenol; 2-methylresorcinol/3-aminophenol; 4-chlororesorcinol/3-aminophenol; resorcinol/5-amino-2-methylphenol; 2-methylresorcinol/5-amino-2-methylphenol; 4-chlororesorcinol/5-amino-2-methylphenol; resorcinol/2-hydroxy-4-aminophenoxyethanol; 2-methylresorcinol/2-hydroxy-4-aminophenoxyethanol; 4-chlororesorcinol/2-hydroxy-4-aminophenoxyethanol; resorcinol/2-amino-3-hydroxypyridine; 2-methylresorcinol/2-amino-3-hydroxypyridines; 4-chlororesorcinol/2-amino-3-hydroxypyridines; resorcinol/3-amino-2-methylamino-6-methoxypyridine; 2-methylresorcinol/3-amino-2-methylamino-6-methoxypyridine; 4-chlororesorcinol/3-amino-2-methylamino-6-methoxypyridine; resorcinol/2,6-dihydroxy-3,4-dimethylpyridine; 2-methylresorcinol/2,6-dihydroxy-3,4-dimethylpyridine, and/or 4-chlororesorcinol/2,6-dihydroxy-3,4-dimethylpyridine, and/or the physiologically acceptable salts thereof.

Preferably agent (B), based on its weight, contains more oxidation dye precursors than agent (A), based on its weight, contains developers.

Methods according to the invention, in which the quantity ratio of the total amount of all oxidation dye precursors of the developer type (a1) in agent (A) to the total amount of all oxidation dye precursors (b1) in agent (B) is a value (a1)/(b1) from 1:1 to 1:10, preferably from 1:2 to 1:8, more preferably from 1:2 to 1:5, and especially preferably from 1:2 to 1:3, are especially preferred.

The ready-to-use agents (B) contain in addition one or more oxidizing agents (b2). Oxidative coloring agents are usually offered in the form of a kit consisting of two components (multicomponent packaging unit), whereby the first component contains the oxidation dye precursors and an alkalinizing agent (for example, ammonia) and the second component contains the oxidizing agent. Peroxides such as, for example, hydrogen peroxide are generally used as oxidizing agents.

The oxidation dye precursors (developer and coupler) themselves are not colored, but the formation of the actual dyes occurs only during the application by the contact of the oxidation dye precursors with the oxidizing agent (preferably hydrogen peroxide). In a chemical reaction, the developers used as oxidation dye precursors (such as, for example, p-phenylenediamine derivatives or p-aminophenol derivatives) are converted by hydrogen peroxide initially oxidatively to a reactive intermediate stage, also called quinoneimine or quinonediimine, which then reacts in an oxidative coupling reaction with the couplers to form the particular dye.

All of the above information on agent (B) refers to the ready-to-use mixture, also if it was obtained only immediately before use from a plurality of formulations (B1), (B2), etc., by mixing.

Persulfates, peroxodisulfates, chlorites, hypochlorites, and particularly hydrogen peroxide and/or one of its stable addition products to organic or inorganic compounds may be suitable as oxidizing agents.

To prevent a premature, undesirable reaction of the oxidation dye precursors with the oxidizing agent, oxidation dye precursors and oxidizing agents are expediently produced separately from one another and brought into contact only immediately before use.

In a further embodiment of the present invention, therefore, agents (B) are preferred, which are characterized in that they are prepared immediately before use by mixing at least two formulations, whereby the at least two formulations are provided in at least two separately produced containers and whereby one container contains a coloring agent (B1), which contains in a cosmetic carrier at least one oxidation dye precursor, and a further container contains an oxidizing agent formulation (B2), containing at least one oxidizing agent.

Preferably, the oxidizing agent formulation (B2) contains hydrogen peroxide as the oxidizing agent and/or one of its stable addition products to organic or inorganic compounds, such as urea, melamine, and sodium borate.

Such oxidizing agent formulations (B2) are preferably aqueous, flowable oxidizing agent formulations. In this case, preferred formulations (B2) are characterized in that the flowable oxidizing agent formulation (B2), based on its weight, contains 40 to 90% by weight, preferably 50 to 85% by weight, especially preferably 55 to 80% by weight, more preferably 60 to 77.5% by weight, and especially 65 to 75% by weight of water.

Preferably, the amount of oxidizing agents in the ready-to-use agent (B) is 0.5 to 12% by weight, preferably 2 to 10% by weight, especially preferably up to 3 to 6% by weight (calculated as 100% $H_2O_2$), in each case based on the ready-to-use agent (B).

In a further preferred embodiment, agent (B) is an agent for coloring and optionally simultaneous lightening of keratinic fibers, which preferably contains 0.5 to 15% by weight, preferably 1 to 12.5% by weight, especially preferably 1.5 to 10% by weight, and especially 2 to 6% by weight of hydrogen peroxide, in each case based on the total weight of the ready-to-use agent (B).

According to the invention, however, the oxidation coloring agent can also be applied to the hair together with a catalyst, which activates the oxidation of the dye precursors. Such catalysts are, e.g., certain enzyme, iodides, quinones, or metal ions.

It has proven advantageous, if the oxidizing agent formulations according to the invention (B2) contain in addition at least one stabilizer or complexing agent for stabilizing the hydrogen peroxide. Especially preferred stabilizers are particularly EDTA and EDDS, and phosphonates, particularly 1-hydroxyethane-1,1-diphosphonate (HEDP), and/or ethylenediamine tetramethylene phosphonate (EDTMP), and/or diethylenetriamine pentamethylene phosphonate (DTPMP), or sodium salts therepf.

To achieve an intensified lightening and bleaching effect, agent (B) can contain furthermore at least one peroxo salt. Suitable peroxo salts are inorganic peroxo compounds, preferably selected from the group comprising ammonium peroxodisulfate, alkali metal peroxodisulfates, ammonium peroxomonosulfate, alkali metal peroxomonosulfates, alkali metal peroxodiphosphates, and alkaline earth metal peroxides. Peroxodisulfates, particularly ammonium peroxodisulfate, potassium peroxodisulfate, and sodium peroxodisulfate are especially preferred.

Agent (B) contains the persulfates in each case in an amount from 0.5 to 20% by weight, preferably 1 to 12.5% by weight, especially preferably 2.5 to 10% by weight, and especially 3 to 6% by weight, based on the total weight of the ready-to-use agent.

Agent (B) can also contain alkalinizing agents; it has proven especially preferable in this regard if agent (B) has a lower pH than agent (A). Suitable methods according to the invention in which agent (A) has a higher pH than agent (B), are preferred because of the higher stabilities of the colors.

The ready-to-use coloring agents (B) furthermore can contain additional active substances, auxiliary substances, and additives in order to improve the coloring performance and to set other desired properties of the agents.

The ready-to-use coloring agents are preferably provided as a liquid formulation and a surface-active substance is therefore added in addition to the agents, whereby such surface-active substances are called surfactants or emulsifiers depending on the field of application: they are preferably selected from anionic, cationic, zwitterionic, amphoteric, and nonionic surfactants and emulsifiers.

Agents preferred according to the invention are characterized in that the agent contains in addition at least one anionic surfactant. Preferred anionic surfactants are fatty acids, alkyl sulfates, alkyl ether sulfates, and ether carboxylic acids having 10 to 20 C atoms in the alkyl group and up to 16 glycol ether groups in the molecule. The anionic surfactants are used in proportions from 0.1 to 45% by weight, preferably 1 to 30% by weight, and very especially preferably from 1 to 15% by weight, based on the total amount of the ready-to-use agent.

Agents preferred according to the invention are characterized in that the agent contains in addition at least one zwitterionic surfactant. Preferred zwitterionic surfactants are betaines, N-alkyl-N,N-dimethylammonium glycinates, N-acylaminopropyl-N,N-dimethylammonium glycinates, and 2-alkyl-3-carboxymethyl-3-hydroxyethylimidazolines. A preferred zwitterionic surfactant is known by the INCI name Cocamidopropyl Betaine.

Agents preferred according to the invention are characterized in that the agent contains in addition at least one amphoteric surfactant. Preferred amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids. Especially preferred amphoteric surfactants are N-cocoalkyl aminopropionate, cocoacylaminoethyl aminopropionate, and $C_{12}$-$C_{18}$ acylsarcosine.

It has proven advantageous furthermore for the agents to contain further non-ionogenic surface-active substances. Preferred nonionic surfactants are, for example, alkylene oxide addition products to fatty alcohols and fatty acids with in each case 2 to 30 mol of ethylene oxide per mole of fatty alcohol or fatty acid. Preparations with excellent properties are likewise obtained if they contain fatty acid esters of ethoxylated glycerol as the nonionic surfactants.

The nonionic, zwitterionic, or amphoteric surfactants are used in proportions from 0.1 to 45% by weight, preferably 1 to 30% by weight, and very especially preferably from 1 to 15% by weight, based on the total amount of the ready-to-use agents.

The ready-to-use coloring agents can contain further auxiliary substances and additives. Thus, it has proven advantageous for the agents to contain at least one thickener. There are no basic restrictions with regard to these thickeners. Both organic and purely inorganic thickeners may be used.

Suitable thickeners are anionic, synthetic polymers; cationic, synthetic polymers; naturally occurring thickeners, such as nonionic guar gums, scleroglucan gums or xanthan gums, gum arabic, gum ghatti, karaya gum, tragacanth gum, carrageenan gum, agar-agar, locust bean flour, pectins, alginates, starch fractions, and derivatives such as amylose, amylopectin, and dextrins, and cellulose derivatives such as, for example, methylcellulose, carboxyalkylcelluloses, and hydroxyalkylcelluloses; nonionic, synthetic polymers such polyvinyl alcohol or polyvinylpyrrolidinone; as well as inorganic thickeners, in particular phyllosilicates such as, for example, bentonite, in particular smectites, such as montmorillonite or hectorite.

The agents according to the invention may also contain zwitterionic polymers.

Preferred zwitterionic polymers are selected from the group comprising:
copolymers of dimethyldiallylammonium salts and acrylic acid, e.g., Polyquaternium-22,
copolymers of dimethyldiallylammonium salts and methacrylic acid,
copolymers of N,N,N-trimethyl-3-[(2-methyl-1-oxo-2-propen-1-yl)amino]-1-propanaminium salts and acrylic acid,
copolymers of N,N,N-trimethyl-3-[(2-methyl-1-oxo-2-propen-1-yl)amino]-1-propanaminium salts and methacrylic acid, copolymers of N,N,N-trimethyl-2-[(2-methyl-1-oxo-2-propen-1-yl)amino]-1-ethanaminium salts and acrylic acid,
copolymers of N,N,N-trimethyl-2-[(2-methyl-1-oxo-2-propen-1-yl)amino]-1-ethanaminium salts and methacrylic acid,
copolymers of N,N,N-trimethyl-3-[(2-methyl-1-oxo-2-propen-1-yl)amino]-1-propanaminium salts, acrylic acid, and acrylamide, e.g., Polyquaternium-53,
copolymers of N,N,N-trimethyl-3-[(2-methyl-1-oxo-2-propen-1-yl)amino]-1-propanaminium salts, methacrylic acid, and acrylamide,
copolymers of 1-ethenyl-3-methyl-1H-imidazolium salts, 1-ethenyl-1H-imidazole, 1-ethenyl-2-pyrrolidinone, and methacrylic acid, e.g., Polyquaternium-86,
copolymers of 1-ethenyl-3-methyl-1H-imidazolium salts, 1-ethenyl-1H-imidazole, 1-ethenyl-2-pyrrolidinone, and acrylic acid.

The agents according to the invention may also contain mixtures of the aforementioned preferred zwitterionic polymers (c).

It turned out, furthermore, that the problem addressed by the invention can be solved particularly completely and in a satisfactory manner, if the agents used in the method according to the invention contain further selected formulation components.

Thus, it became apparent that the additional presence of certain, higher-chain fatty alcohols improves the color result of the formulations according to the invention still further. Therefore, it is preferred if the agents used in the method according to the invention contain in addition one or more fatty alcohols from the group comprising arachyl alcohol (eisocan-1-ol), gadoleyl alcohol ((9Z)-eicos-9-en-1-ol), arachidonic alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and brassidyl alcohol ((13E)-docosen-1-ol).

Especially suitable agents contain one or more higher-chain alcohols of the aforementioned group in a total amount from 1.0 to 10.0% by weight, preferably from 1.4 to 8.0% by weight, more preferably from 1.8 to 6.0% by weight, and especially preferably from 2.0 to 4.0% by weight, based on the total weight of the ready-to-use agent.

In a further preferred embodiment, an agent used in the method according to the invention is therefore characterized in that it contains in addition one or more fatty alcohols from the group comprising arachyl alcohol (eisocan-1-ol), gadoleyl alcohol ((9Z)-eicos-9-en-1-ol), arachidonic alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and brassidyl alcohol ((13E)-docosen-1-ol) in a total amount from 0.1 to 10.0% by weight, preferably from 1.4 to 8.0% by weight, more preferably from 1.8 to 6.0% by weight, and especially preferably from 2.0 to 4.0% by weight, based on the total weight of the ready-to-use agent.

It turned out that a pretreatment at slightly elevated temperatures allows the multi-tonal effects to be still more vibrant. Methods preferred according to the invention are characterized in that agent (A) in step B) is allowed to act at a temperature of at least 40° C.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for the oxidative dyeing of keratinic fibers, comprising:
   A) applying a cosmetic agent (A) to the fibers,
   B) allowing agent (A) to act for a time period from 30 seconds to 30 minutes,
   C) applying a cosmetic agent (B) to the keratinic fibers still being acted upon by agent (A),
   D) allowing both agents (A) and (B) to act for a time period from 5 to 45 minutes, and
   E) rinsing out of agents (A) and (B),
   wherein
   agent (A)
   (a1) contains one or more oxidation dye precursors of the developer type,
   (a2) does not contain an oxidation dye precursor of the coupler type,
   (a3) has a pH from 8.0 to 12.0, and
   agent (B)
   (b1) contains one or more oxidation dye precursors,
   (b2) contains one or more oxidizing agents, and
   (b3) has a pH from 8.0 to 12.0.

2. The method according to claim 1, wherein agent (A) contains as an oxidation dye precursor of the developer type (a1) one or more compounds selected from the group consisting of p-phenylenediamine, p-toluylenediamine, 2-(2-hydroxyethyl)-p-phenylenediamine, 2-(1,2-dihydroxyethyl)-p-phenylenediamine, N,N-bis(2-hydroxyethyl)-p-phenylenediamine, 2-methoxymethyl-p-phenylenediamine, N-(4-amino-3-methylphenyl)-N-[3-(1H-imidazol-1-yl)propyl]amine, and the physiologically acceptable salts thereof in a total amount from 0.1 to 3.5% by weight based on the total weight of agent (A).

3. The method according to claim 1, wherein agent (A) contains as an oxidation dye precursor of the developer type (a1) one or more compounds selected from the group consisting of bis(2-hydroxy-5-aminophenyl)methane, 1,3-bis(2,5-diaminophenoxy)propan-2-ol, N,N'-bis(4-aminophenyl)-1,4-diazacycloheptane, 1,10-bis(2,5-diaminophenyl)-1,4,7,10-tetraoxadecane, p-aminophenol, 4- and amino-3-methylphenol, and the physiologically acceptable salts thereof in a total amount from 0.1 to 3.5% by weight based on the total weight of agent (A).

4. The method according to claim 1, wherein agent (A) contains as an oxidation dye precursor of the developer type (a1) one or more compounds selected from the group consisting of 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, and the physiologically acceptable salts thereof in a total amount from 0.1 to 3.5% by weight based on the total weight of agent (A).

5. The method according to claim 1, wherein agent (A) contains as oxidation dye precursors of developer type (a1) at least one combination selected from the group consisting of: p-toluylenediamine/2-(2-hydroxyethyl)-p-phenylenediamine; p-toluylenediamine/2-methoxymethyl-p-phenylenediamine; p-toluylenediamine/N,N-bis(2-hydroxyethyl)-p-phenylenediamine; p-toluylenediamine/2-methoxymethyl-p-phenylenediamine; p-toluylenediamine/N-(4-amino-3- methylphenyl)-N-[3-(1H-imidazol-1-yl)propyl]amine; p-toluylenediamine/bis(2-hydroxy-5-aminophenyl)methane; p-toluylenediamine/4- and amino-3-methylphenol; p-toluylenediamine/4,5-diamino-1-(2-hydroxyethyl)pyrazole; p-toluylenediamine/2,4,5,6-tetraaminopyrimidine; 2-(2-hydroxyethyl)-p-phenylenediamine/2-methoxymethyl-p-phenylenediamine; 2-(2-hydroxyethyl)-p-phenylenediamine/N,N-bis(2-hydroxyethyl)-p-phenylenediamine; 2-(2-hydroxyethyl)-p-phenylenediamine/2-methoxymethyl-p-phenylenediamine; 2-(2-hydroxyethyl)-p-phenylenediamine/N-(4-amino-3-methylphenyl)-N-[3-(1H-imidazol-1-yl)propyl]amine; 2-(2-hydroxyethyl)-p-phenylenediamine/bis(2-hydroxy-5-aminophenyl)methane; 2-(2-hydroxyethyl)-p-phenylenediamine/4-amino-3-methylphenol; 2-(2-hydroxyethyl)-p-phenylenediamine/4,5-diamino-1-(2-hydroxyethyl)pyrazole; 2-(2-hydroxyethyl)-p-phenylenediamine/2,4,5,6-tetraaminopyrimidine; 2-methoxymethyl-p-phenylenediamine/2-(2-hydroxyethyl)-p-phenylenediamine; 2-methoxymethyl-p-phenylenediamine/2-methoxymethyl-p-phenylenediamine; 2-methoxymethyl-p-phenylenediamine/N,N-bis(2-hydroxyethyl)-p-phenylenediamine; 2-methoxymethyl-p-phenylenediamine/2-methoxymethyl-p-phenylenediamine; 2-methoxymethyl-p-phenylenediamine/N-(4-amino-3-methylphenyl)-N-[3-(1H-imidazol-1-yl)propyl]amine; 2-methoxymethyl-p-phenylenediamine/bis(2-hydroxy-5-aminophenyl)methane; 2-methoxymethyl-p-phenylenediamine/4-amino-3-methylphenol; 2-methoxymethyl-p-phenylenediamine/4,5-diamino-1-(2-hydroxyethyl)pyrazole; 2-methoxymethyl-p-phenylenediamine/2,4,5,6-tetraaminopyrimidine, 4- and amino-3-methylphenol/4,5-diamino-1-(2-hydroxyethyl)pyrazole, and the physiologically acceptable salts thereof.

6. The method according to claim 1, wherein agent (A) has a pH (a3) from 8.5 to 11.5.

7. The method according to claim 1, wherein agent (A) contains one or more alkalinizing agents selected from the group consisting of sodium hydroxide, potassium hydroxide, ammonia, monoethanolamine, and 2-amino-2-methylpropanol in a total amount from 0.3 to 4.5% by weight based on the total weight of agent (A).

8. The method according to claim 1, wherein agent (A) in step B) is allowed to act on the fibers for a time period from 30 seconds to 15 minutes.

9. The method according to claim 1, wherein agent (A) contains in addition at least one thickener and/or at least one gelling agent.

10. The method according to claim 1, wherein agent (B) contains as an oxidation dye precursor (b1) one or more oxidation dye precursors of the developer type.

11. The method according to claim 10, wherein agents (A) and (B) contain the same oxidation dye precursors of the developer type.

12. The method according to claim 10, wherein agents (A) and (B) contain different oxidation dye precursors of the developer type.

13. The method according to claim 1, wherein the quantity ratio of the total amount of all oxidation dye precursors of the developer type (a1) in agent (A) to the total amount of all oxidation dye precursors (b1) in agent (B) is a value (a1)/(b1) from 1:1 to 1:10.

14. The method according to claim 1, wherein agents (A) and (B) in step D) are allowed to act for a time period from 5 to 30 minutes.

15. The method according to claim 1, wherein agent (A) has a higher pH than agent (B).

* * * * *